(12) United States Patent
Stamm et al.

(10) Patent No.: US 6,734,322 B1
(45) Date of Patent: May 11, 2004

(54) METHOD FOR PRODUCING O-CHLOROMETHYL BENZENECARBONYL CHLORIDES

(75) Inventors: Armin Stamm, Mainz (DE); Roland Götz, Neulussheim (DE); Norbert Götz, Worms (DE); Jochem Henkelmann, Mannheim (DE); Heinz-Josef Kneuper, Niederkirchen (DE); Bernd Wolf, Fussgönheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 34 days.

(21) Appl. No.: 10/130,826
(22) PCT Filed: Nov. 27, 2000
(86) PCT No.: PCT/EP00/11814
§ 371 (c)(1), (2), (4) Date: May 23, 2002
(87) PCT Pub. No.: WO01/42183
PCT Pub. Date: Jun. 14, 2001

(30) Foreign Application Priority Data

Dec. 6, 1999 (DE) .......................... 199 58 601

(51) Int. Cl.$^7$ ............................... C07C 51/58
(52) U.S. Cl. ..................... 562/857; 549/307
(58) Field of Search ............... 562/840, 856, 562/857, 861, 864

(56) References Cited

U.S. PATENT DOCUMENTS 5,130,478 A * 7/1992 Gauthier et al. ............ 562/857

FOREIGN PATENT DOCUMENTS

| EP | 583 589 | 2/1994 |
| WO | 97/12854 | 4/1997 |
| WO | 99/16743 | 4/1999 |

* cited by examiner

*Primary Examiner*—Porfirio Nazario-Gonzalez
*Assistant Examiner*—Karl Puttlitz
(74) *Attorney, Agent, or Firm*—Keil & Weinkauf

(57) ABSTRACT

The invention relates to a method for producing o-choromethyl benzenecarbonyl chlorides of formula (I), wherein $R^1$–$R^4$ can be the same or different and stand for hydrogen, $C_1$–$C_4$-alkyl, halogen or trifluoromnethyl, by converting benzocondensed lactones of formula (II), wherein $R^1$–$R^4$ have the aforementioned meaning, with gaseous or liquid phosgene and the dimers or trimers thereof. The inventive method is characterized in that the conversion is carried out in the presence of catalytical amounts of a Lewis acid and catalytical amounts of a phosgenation catalyst

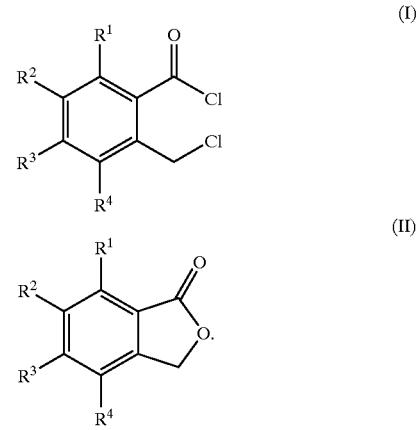

10 Claims, No Drawings

METHOD FOR PRODUCING O-CHLOROMETHYL BENZENECARBONYL CHLORIDES

The present invention relates to a process for preparing o-chloromethylbenzoyl chlorides of the formula I,

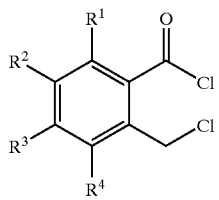

in which $R^1$ to $R^4$ are as defined above, with gaseous or different and are hudrogen, $C_1$–$C_4$-alkyl, halogen or trifluoromethyl, by reacting benzo-fused lactones of the formula II

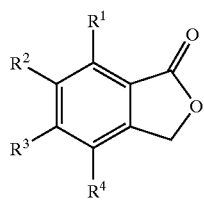

in which $R^1$ to $R^4$ are as defined above, with gaseous or liquid phosgene, its dimers or trimers. liquid phosgene, its dimers or trimers.

TECHNICAL FIELD o-chloromethyl-substituted benzoyl chlorides are important intermediates for preparing, for example, pesticidally active compounds as described in the patents EP-A 460 575, EP-A 463 488, WO-A 95/18789, WO-A 95/21154 and WO-A 97/15552.

o-Chloromethyl-substituted benzoyl chlorides can be prepared, for example, by reacting benzo-fused lactones with thionyl chloride or phosgene.

BACKGROUND ART

EP-A 676 389 describes the preparation of o-chloromethylbenzoyl chlorides from benzo-fused lactones using thionyl chloride in the presence of a catalyst. To achieve complete conversion, reaction temperatures of 160–170° C. are required, at which thionyl chloride is already partially decomposed, resulting in the formation of troublesome byproducts.

In WO-A 99/16743, the reaction with thionyl chloride is carried out in the presence of a quaternary ammonium salt and a Lewis acid at 90–100° C. However, quaternary ammonium salts are problematic from an environmental point of view and have the following technical disadvantages: owing to sublimation, parts of the plants may become blocked. Furthermore, the salts are hygroscopic, which may lead to water being introduced and to a higher consumption of chlorinating agent. Finally, the ammonium salts interfere with the distillative purification of the o-chloromethylbenzoyl chlorides.

Carrying out the reaction using thionyl chloride as chlorinating agent is disadvantageous since sulfur dioxide, which has to be worked-up or neutralized, is formed as coproduct in the synthesis. If the chlorinating agent used is phosgene, carbon dioxide, which does not have to be disposed of, is the only byproduct.

EP-A 583 589 describes a process for preparing o-chloromethylbenzoyl chlorides by phosgenation of benzo-fused lactones in the presence of a catalyst at 170–180° C. In contrast to thionyl chloride, phosgene is thermally stable under these conditions; however, the handling of phosgene and its hold up in the condenser at the high temperatures involved is made more difficult by increased safety precautions. Furthermore, under these conditions, the reaction product is under high thermal stress, which may result in its partial decomposition.

In WO 97/12854, triarylphosphine oxides are used as special catalyst type for the reaction, owing to which the use of hydrogen chloride can be dispensed with; however, this does not result in an improvement in the required reaction conditions with respect to the objectionably high reaction temperatures and the resulting safety precautions required.

DISCLOSURE OF INVENTION

It is an object of the present invention to provide an economical process, capable of being carried out on an industrial scale, for preparing o-chloromethylbenzoyl chlorides which does not have the abovementioned disadvantages and still affords high yields.

We have found that this object is achieved by the process mentioned at the outset, which comprises carrying out the reaction with phosgene, its dimers or trimers in the presence of catalytic amounts of a Lewis acid and catalytic amounts of a phosgenation catalyst.

The starting materials used are benzo-fused lactones (phthalides) of the formula II,

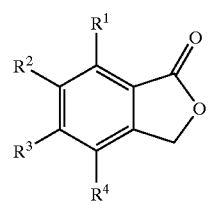

in which $R^1$ to $R^4$ can be identical or different and are hydrogen (H), $C_1$–$C_4$-alkyl, halogen (fluorine, chlorine, bromine or iodine) or trifluoromethyl. Preference is given to using unsubstituted phthalide.

The chlorinating agent used is preferably gaseous or liquid phosgene. Furthermore, it is also possible to use dimers (trichloromethyl chloroformate, "diphosgene") or trimers of phosgene (bistrichloromethyl carbonate, "triphosgene") or mixtures of these chlorinating agents.

Suitable phosgenation catalysts are, in particular, nitrogen compounds and phosphorus compounds. Examples which can be considered are N,N-disubstituted formamides, hexaalkylguanidinium salts, trialkylphosphines or triarylphosphines which may be substituted or unsubstituted in the aryl moiety, trialkylphosphine oxides or triarylphosphine oxides which may be substituted or unsubstituted in the aryl moiety, N-substituted imidazoles and substituted or unsubstitited pyridines. Particular preference is given to the pyridines of the formula IIIa,

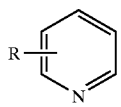

IIIa where R is hydrogen or methyl, and to phosphine oxides of the formula IIIb,

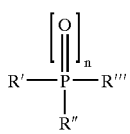

IIIb in which $R^1$ to $R'''$ can be identical or different and are $C_1$–$C_{10}$-alkyl or unsubstituted or $C_1$–$C_4$-alkyl-substituted phenyl and the index n is 0 or 1. Particular preference is given to 3-methylpyridine (β-picoline) and unsubstituted triphenylphosphine oxide.

The use of liquid trialkylphosphine oxides has, in particular, technical advantages (no need to handle solids, easier discharge of the distillation residue during purification). The tri-$C_6$–$C_8$-alkylphosphine oxides available under the trade name Cyanex® (for example. Cyanex® 923 from Cyanamide) are, for example, suitable here. Liquid trialkylphosphine oxides combined with Lewis acids, such as tri($C_1$–$C_4$-alkyl) borates and boric acid, have been found to be particularly useful.

The phosgenation catalyst is generally added in amounts of from 0.1 to 20 mol %, based on the amount of benzo-fused lactone used, and is preferably added in amounts of from 1 to 10 mol %.

Suitable Lewis acids are, in particular, boron compounds, such as, in particular, $BF_3$, $BCl_3$ or complexes thereof with oxygen compounds, sulfur compounds or nitrogen compounds, tri($C_1$–$C_4$-alkyl) borates and boric acid ($H_3BO_3$) itself. Furthermore suitable are $AlCl_3$, alkylaluminum dichlorides and dialkylaluminum chlorides, and heterogeneous Lewis-acidic alumosilicates of the zeolite type. Particular preference is given to $BF_3$, $BCl_3$ and complexes thereof with ether (in particular diethyl ether), water (dihydrate), alcohol (in particular methanol), sulfide (in particular dimethyl sulfide) and amine (in particular ethylamine). Particularly suitable are, for example, $BF_3$ etherate and $BF_3$ dihydrate.

The Lewis acid used is particularly preferably boric acid or tri($C_1$–$C_4$-alkyl) borate. Such processes give excellent yields and have the advantage that the reaction mixtures are free from fluoride ions. Compared to the analogous reaction where the Lewis acid used is $BF_3$, the entire apparatus can be simplified.

The Lewis acid is added in amounts of from 0.1 to 20 mol %, based on the amount of benzo-fused lactone used, preferably in amounts of from 0.5 to 5 mol %.

In a further preferred embodiment of the process, the catalyst used is a complex, formed beforehand, of Lewis acid and the phosgenation catalyst. In general, this complex is employed in a concentration of from 0.1 to 20 mol %, based on the amount of benzo-fused lactone used. The catalyst used is preferably a complex of $BF_3$ and a methyl-substituted pyridine, and particular preference is given to the $BF_3$-β-picoline complex.

If desired, hydrogen chloride can be introduced in parallel to the introduction of phosgene, to accelerate ring-opening. However, the introduction of hydrogen chloride during the synthesis is preferably dispensed with.

Furthermore, it may be advantageous to employ heterogeneous Lewis-acidic catalysts, such as, for example, zeolites of the faujasite type in which some or all of the exchangeable cations have been replaced by protons. A heterogeneously catalyzed reaction has the advantage that it can be carried out in a fixed bed. The heterogeneous catalyst is employed in amounts of from 0.01 to 10% by weight and preferably in amounts of from 0.1 to 1% by weight, based on the amount of benzo-fused lactone used.

The reaction temperature is generally 110–200° C. and preferably 130–160° C.

The process is preferably carried out in the absence of a solvent. However, it is possible to add a solvent which is inert to phosgene. Inert solvents are, for example, aromatic hydrocarbons, such as toluene, o-, m- or p-xylene or mixtures thereof, chlorinated aromatic hydrocarbons, such as chlorobenzene or dichlorobenzenes, or cyclic carbonates, such as ethylene carbonate or propylene carbonate.

The process can be carried out either continuously or batchwise.

MODE(S) FOR CARRYING OUT THE INVENTION

The examples below serve to illustrate the process in more detail.

General process description for all examples:

In a phosgenation apparatus consisting of a 1 l double-jacketed reactor fitted with a battery of high-efficiency condensers, in each case 2 mol (268 g) of phthalide were initially charged and molten together with the catalyst system in question. After heating to 140° C., gaseous phosgene was introduced until no more phosgene was consumed (noticeable by a decrease in the internal temperature). The mixture was then stirred at 140° C. for 1 hour, and excess phosgene was then stripped at 100° C. using nitrogen. In selected examples, the product was isolated by fractional distillation at 1 mbar and 93–95° C.

EXAMPLE 1

9.3 g (0.1 mol, 5 mol %) of β-picoline (3-methylpyridine) and 7.9 g (0.04 mol, 2 mol %) of $BF_3$-diethyl ether complex ("$BF_3$-etherate") were added as catalyst. Over a period of 8 h, a total of 218 g (2.18 mol) of gaseous phosgene were introduced at 140–145° C. After the excess phosgene had been stripped, the reaction discharge (387 g) contained 95 GC area % of o-chloromethylbenzoyl chloride and 2.5 GC area % of unreacted phthalide. Distillation of the crude discharge gave 350 g of o-chloromethylbenzoyl chloride (93% of theory) of a purity of 97%.

EXAMPLE 2

392 g (3 mol) of phthalide together with 14 g (0.15 mol) of β-picoline and 12 g (0.06 mol) of $BF_3$ etherate were heated to 140° C. At 140–145° C., a total of 342 g (3.42 mol) of gaseous phosgene were introduced. After an extra reaction time of 1 h, the excess phosgene was stripped using nitrogen. The reaction discharge (572 g) contained 97 GC area % of o-chloromethylbenzoyl chloride and 1 GC area % of phthalide.

EXAMPLE 3

The catalyst added comprised 20 g of a $BF_3$-p-picoline complex, which had been prepared beforehand. Over a period of 6 h, a total of 230 g (2.3 mol) of gaseous phosgene were introduced. After the excess phosgene had been stripped, the reaction discharge (391 g) contained 97.2 GC area % of o-chloromethylbenzoyl chloride and 0.7 GC area % of phthalide. Distillation of the crude discharge gave 334 g of o-chloromethylbenzoyl chloride (88% of theory) of a purity of 98.8%.

EXAMPLE 4

2 mol of phthalide (268 g) were initially charged with 27.8 g of triphenylphosphine oxide (TPPO) (0.1 mol) and 1 g of HY zeolite GE 1967. At 140–149° C., a total of 231 g of gaseous phosgene (2.31 mol) were introduced over a period of 8 h. After an extra stirring time of 1 h at 140° C., the excess phosgene was stripped using nitrogen. The discharge (403 g) contained 78 GC area % of o-chloromethylbenzoyl chloride and 6.8% of phthalide.

EXAMPLE 5

2 mol of phthalide (268 g) were initially charged with 27.8 g of TPPO (0.1 mol) and 7.9 g (0.04 mol) of BF3 etherate. At 140–150° C., a total of 233 g of gaseous phosgene (2.33 mol) were introduced over a period of 8 h. After an extra stirring time of 1 h at 140° C., the excess phosgene was stripped using nitrogen. The discharge (415 g) contained 88.4 GC area % of o-chloro-methylbenzoyl chloride and 0.1% of phthalide. Fractional distillation of the crude discharge gave 363 g (96% of theory) of o-chloromethylbenzoyl chloride of a purity of 99.8%.

EXAMPLE 6

268 g (2 mol) of phthalide, 9.3 g (0.1 mol) of β-picoline and 50 ml of a 0.1 molar solution of $BCl_3$ in xylene were initially charged. At 140–150° C., a total of 200 g (2 mol) of gaseous phosgene was introduced over a period of 8 h. The mixture was then stirred at 140° C. for another hour. Excess phosgene was stripped using nitrogen, giving a discharge of 398 g having a content of 77.2 GC area % of o-chloromethylbenzoyl chloride and 10.9% of unreacted phthalide.

EXAMPLE 7

268 g (2 mol) of phthalide, 9.3 g (0.1 mol) of β-picoline and 3.1 g (0.05 mol) of crystalline boric acid (Riedel de Haen) were initially charged. At 140–150° C., a total of 245 g (2.45 mol) of gaseous phosgene was introduced over a period of 7 h. The mixture was then stirred at 140° C. for another hour. Excess phosgene was stripped using nitrogen, giving a discharge of 380 g having a content of 96 GC area % of o-chloro-ethylbenzoyl chloride and 1.4% of unreacted phthalide. ractional distillation of the crude discharge gave 340 g of o-chloromethylbenzoyl chloride (90% of theory) of a purity of >97%.

EXAMPLE 8

268 g (2 mol) of phthalide, 27.8 g (0.1 mol) of TPPO and 3.1 g (0.05 mol) of crystalline boric acid (Riedel de Haën) were initially charged. At 140–150° C., a total of 247 g (2.47 mol) of gaseous phosgene was introduced over a period of 5 h 45 min. The mixture was then stirred at 140° C. for another hour. Excess phosgene was stripped using nitrogen, giving a discharge of 411 g having a content of 88 GC area % of o-chloromethylbenzoyl chloride and 0.7% of unreacted phthalide. Fractional distillation of the crude discharge gave 358 g of o-chloromethylbenzoyl chloride (94% of theory) of a purity of 98.5%.

EXAMPLE 9

268 g (2 mol) of phthalide, 27.8 g (0.1 mol) of TPPO and 5.2 g (0.05 mol) of trimethyl borate (Aldrich) were initially charged. At 140–150° C., a total of 256 g (2.56 mol) of gaseous phosgene was introduced over a period of 7 h. The mixture was then stirred at 140° C. for another hour. Excess phosgene was stripped using nitrogen, giving a discharge of 410 g having a content of 87.6 GC area % of o-chloromethylbenzoyl chloride and 1.1% of unreacted phthalide.

EXAMPLE 10

2 mol of phthalide, 34.8 g (0.1 mol) of cyanex 923 (Cyanamid) and 3.1 g (0.05 mol) of boric acid were initially charged. At 141 to 150° C., a total 257 g (2.57 mol) of phosgene was introduced over a period of 4 h. The mixture was stirred at 140° C. for another hour, and excess phosgene was stripped using nitrogen. The crude discharge of 417 g was subjected to fractional distillation. This gave 352 g (93% of theory) of o-chloromethylbenzoyl chloride of a purity of 98.7%.

EXAMPLE 11

2 mol of phthalide, 34.8 g (0.1 mol) of Cyanex 923 (Cyanamid) and 5.2 g (0.05 mol) of trimethyl borate were initially charged. At 141 to 150° C., a total of 244 g (2.44 mol) of phosgene was introduced over a period of 6 h. The mixture was stirred at 140° C. for another hour, and excess phosgene was stripped using nitrogen. The crude discharge of 411 g was subjected to fractional distillation. This gave 357 g (94% of theory) of o-chloromethylbenzoyl chloride of a purity of 97.7%.

Comparative Example I Compared to WO-A 99/16743

According to the general experimental procedure, 9.1 g of triethylbenzylammonium chloride (TEBA) (0.04 mol, 2 mol %) and 7.9 g of $BF_3$ etherate (0.04 mol, 2 mol %) were used as catalyst mixture. Over a period of 11 h, a total of 45 g (0.45 mol) of gaseous phosgene was introduced at a reaction temperature of initially 95–100° C. (3 h) and then at 140°C. After an extra reaction time of 1 h at 140° C. and stripping of the phosgene, the crude discharge contained only 7.7 GC area % of o-chloromethylbenzoyl chloride and 91% of unreacted phthalide.

Comparative Example I shows that the phosgenation reaction cannot be carried out under the conditions preferred in WO 99/16743.

Comparative Example II Compared With EP-A 583 589

2 mol of phthalide were initially charged with 18.6 g of β-picoline (0.2 mol, 10 mol %). At 142–152° C. 209 g (2.1 mol) of gaseous phosgene and 154 g of gaseous HCl were introduced in parallel over a period of 10 h. After an extra stirring time and stripping of excess phosgene, the reaction discharge (380 g) contained 86% of o-chloromethylbenzoyl chloride and 6% of unreacted phthalide.

Comparative Example II shows that without the addition of a Lewis acid, the reaction proceeds considerably more slowly and with a poorer yield, and that furthermore more phosgenation catalyst is required.

We claim:

1. A process for preparing o-chloromethylbenzoyl chlorides of the formula I

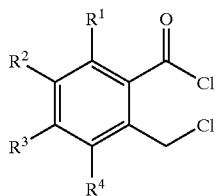

in which $R^1$ to $R^4$ can be identical or different and are hydrogen, $C_1$–$C_4$-alkyl, halogen or trifluoromethyl, by reacting benzo-fused lactones of the formula II

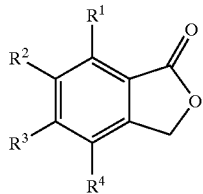

in which $R^1$ to $R^4$ are as defined above with gaseous or liquid phosgene, its dimers or trimers, which comprises carrying the reaction in the presence of catalytic amounts of a Lewis acid and catalytic amounts of a phosgenation catalyst, and wherein the Lewis acid is selected from the group consisting of: boron compounds, aluminum trichloride, alkylaluminum dichlorides, dialkylaluminum chlorides and alumosilicates of the zeolite type.

2. A process as claimed in claim 1, wherein the Lewis acid used is a boron compound.

3. A process as claimed in claim 2, wherein the Lewis acid used is boron trifluoride or boron trifluoride in coordinate form.

4. A process as claimed in claim 2, wherein the Lewis acid used is boric acid or a tri-$C_1$–$C_4$-alkyl borate.

5. A process as claimed in claim 1, wherein the Lewis acid used is an alumosilicate of the zeolite type.

6. A process as claimed in claim 1, wherein the Lewis acid is employed in a concentration of from 0.1 to 20 mol %, based on the lactone II.

7. A process as claimed in claim 1, wherein the catalyst used is from 0.1 to 20 mol % of a complex of Lewis acid and phosgenation catalyst.

8. A process as claimed in claim 1, wherein the phosgenation catalyst used is a pyridine of the formula IIIa or a phosphine (oxide) of the formula IIIb,

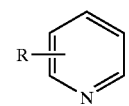

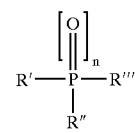

where in the formula IIIa, R is hydrogen or methyl, and in the formula IIIb, R' to R''' can be identical or different and are $C_1$–$C_{10}$-alkyl or unsubstituted or $C_1$–$C_4$-alkyl-substituted phenyl and the index n is 0 or 1.

9. A process as claimed in claim 8, wherein the phosgenation catalyst used is 3-methylpiperidine (β-picoline), triphenyl-phosphine oxide or a liquid trialkylphosphine oxide.

10. A process as claimed in claim 1, wherein from 0.1 to 20 mol % of the phosgenation catalyst, based on lactone II, are used.

* * * * *